United States Patent [19]

Aasen et al.

[11] Patent Number: 4,719,149

[45] Date of Patent: Jan. 12, 1988

[54] METHOD FOR PRIMING HARD TISSUE

[75] Inventors: Steven M. Aasen, Lakeland; Joel D. Oxman, St. Louis Park, both of Minn.

[73] Assignee: Minnesota Mining and Manufacturing Company, St. Paul, Minn.

[21] Appl. No.: 835,034

[22] Filed: Feb. 28, 1986

[51] Int. Cl.$^4$ .................. C09K 3/00; A61C 5/04; A61K 6/08; B32B 9/02
[52] U.S. Cl. ..................... 428/473; 106/35; 427/2; 433/226; 523/116
[58] Field of Search .............. 106/35; 427/2; 433/226; 523/116; 428/473

[56] References Cited

U.S. PATENT DOCUMENTS

| | | | |
|---|---|---|---|
| 3,200,142 | 8/1965 | Bowen | 260/486 |
| 3,882,600 | 5/1975 | Plymale | 32/15 |
| 3,954,475 | 5/1976 | Bonham et al. | 96/67 |
| 3,997,504 | 12/1976 | Plymale | 260/42.27 |
| 4,182,035 | 1/1980 | Yamauchi et al. | 433/228 |
| 4,212,970 | 7/1980 | Iwasaki | 542/455 |
| 4,222,780 | 9/1980 | Shibatani et al. | 106/35 |
| 4,235,633 | 11/1980 | Tomioka et al. | 106/35 |
| 4,259,075 | 3/1981 | Yamauchi et al. | 433/217 |
| 4,259,117 | 3/1981 | Yamauchi et al. | 106/35 |
| 4,368,043 | 1/1983 | Yamauchi et al. | 433/217 |
| 4,382,782 | 5/1983 | Smith et al. | 433/217 |
| 4,383,052 | 5/1983 | Higo et al. | 523/118 |
| 4,404,150 | 9/1983 | Tsunekawa et al. | 260/927 |
| 4,443,197 | 4/1984 | Fusayama et al. | 433/217 |
| 4,499,251 | 2/1985 | Omura et al. | 526/278 |
| 4,514,342 | 4/1985 | Billington et al. | 260/952 |
| 4,515,930 | 5/1985 | Omura et al. | 526/276 |
| 4,518,430 | 5/1985 | Brown et al. | 106/35 |
| 4,521,550 | 6/1985 | Bowen | 523/116 |
| 4,525,511 | 6/1985 | Kirby et al. | 524/158 |
| 4,535,102 | 8/1985 | Kusumoto et al. | 523/116 |
| 4,537,940 | 8/1985 | Omura et al. | 526/278 |
| 4,538,990 | 9/1985 | Pashley | 433/217 |
| 4,539,382 | 9/1985 | Omura et al. | 526/276 |
| 4,544,467 | 10/1985 | Bunker et al. | 204/159.24 |
| 4,553,941 | 11/1985 | Aasen | 433/228.1 |
| 4,588,756 | 5/1986 | Bowen | 523/116 |
| 4,591,649 | 5/1986 | Hirasawa et al. | 549/232 |
| 4,593,054 | 6/1986 | Asmussen et al. | 523/118 |
| 4,645,456 | 8/1986 | James | 433/217.1 |

FOREIGN PATENT DOCUMENTS

| | | |
|---|---|---|
| 4893-83 | 10/1983 | Denmark . |
| 0058483 | 8/1982 | European Pat. Off. . |
| 0155812 | 9/1985 | European Pat. Off. . |
| 2711234 | 9/1977 | Fed. Rep. of Germany ...... 523/116 |
| 31754 | 3/1974 | Japan ................... 523/116 |
| 57-143372 | 9/1982 | Japan . |
| 57-167364 | 10/1982 | Japan . |

OTHER PUBLICATIONS

M. Buonocore, W. Wileman, and F. Brudevold, *J. Dent. Res.*, 35, 846, (1956).
M. Buonocore and M. Quigley, *J. Amer. Dent. Assoc.*, 57, 807, (1958).
Public Health Service Publication No. 1494, "Adhesive Restoration Dental Materials—II", pp. 103–155, (1966).
M. Buonocore, "The Challenge of Bonding to Dentin", *The Acid Etch Technique*, (St. Paul, 1974).
N. Nakabayashi, K. Kojima, and E. Masuhara, *J. Bio. Mat. Res.*, 16, 265–273, (1982).
K. Nagata, T. F. Lundeen, and P. T. Turner, *J. Bio. Mat. Res.*, 18, 1089–1103, (1984).
R. L. Bowen, R. L. Blosser, and A. D. Johnston, Abstract No. 915, p. 276, AIDR/AADR Abstracts, 1985, (Paper presented Mar. 22, 1985).
E. C. Munksgaard and E. Asmussen, *J. Dent. Res.*, 63, (8): 1087–1089, (1984).
E. C. Munksgaard, M. Irie, and E. Asmussen, *J. Dent. Res.*, 64, (12:1409–1411), (1985).
M. Buonocore, *J. Dent. Res.*, 34, 849, (1955).
E. Asmussen and E. C. Munksgaard, *Scand. J. Dent. Res.*, 92, 480, (1984).
E. C. Munksgaard, E. K. Hansen and E. Asmussen, *Scand. J. Dent. Res.*, 92, 544, (1984).
E. C. Munksgaard, K. Itoh, and K. D. Jorgensen, *J. Dent. Res.*, 64(2):144–146, (1985).
E. Asmussen and E. C. Munksgaard, "Adhesion of Restorative Resins to Dentinal Tissues"; D. R. Beech, Bonding of Restorative Resins to Dentin; Open Discussion of Asmussen/Beech Papers, *Posterior Composite Resin Dental Restorative Materials, pp. 217–241, (1985)*.
Lee Pharmaceutical Technical Bulletin No. 2200, (dated "11-1-84"); No. 2400, (dated "11-30-85").
"Eliminate the Acid Etch from Your Direct Bonding", (Brochure of Lee Pharmaceuticals, undated).
"Lee Cleanse & Bond I Application Procedure With Elapsed Times: (Brochure of Lee Pharmaceuticals, undated).
Welcher, F. J., *The Analytical Uses of Ethylenediamine Tetraacetic Acid*, pp. 6–7, (1958).

*Primary Examiner*—Michael R. Lusignan
*Attorney, Agent, or Firm*—Donald M. Sell; James A. Smith; David R. Cleveland

[57] ABSTRACT

An acid and a water-soluble film former are used as a primer for hard tissue (e.g., dentin). The acid has a p$K_a$ less than or equal to that of phenol and the acid and its calcium salt(s) are soluble in the film former. The primer is free of adhesively detrimental quantities of calcium salts that are not soluble in the film former.

22 Claims, No Drawings

METHOD FOR PRIMING HARD TISSUE

TECHNICAL FIELD

This invention relates to a method for priming hard tissue. This invention also relates to primer compositions for use on hard tissue.

BACKGROUND ART

In recent years there has been intense interest in the dental field in adhesives that bond to hard tissues such as dentin. Many of these adhesives have been used in conjunction with an acid pretreatment of the dentin prior to application of the adhesive. A very wide variety of acids have been tried, with phosphoric, citric and oxalic acids being particularly popular pretreatments. The use of such acids, especially phosphoric acid, has not been without controversy. The American Dental Association has recommended against phosphoric acid pretreatment of dentin. However, phosphoric acid is extensively used as a pretreatment in Japan in conjunction with dentin adhesives from Kuraray Company, Ltd. Citric acid has a less severe etching effect than phosphoric acid and is used as a dentin pretreatment in the U.S. in conjunction with a dentin adhesive sold by Den-Mat Corporation. Oxalic acid also has a less severe etching effect than phosphoric acid, and the use of its monoacid and certain of its salts as a pretreatment is described in U.S. Pat. No. 4,538,990. Other references describing various pretreatments for dentin include M. Buonocore, W. Wileman, and F. Brudevold, *J. Dent. Res.*, 35, 846 (1956), M. Buonocore and M. Quigley, *J. Amer. Dent. Assoc.*, 57, 807 (1958), Public Health Service Publication No. 1494, "Adhesive Restorative Dental Materials—II", pp. 103-155 (1966), M. Buonocore, "The Challenge of Bonding to Dentin", *The Acid Etch Technique*, (St. Paul, 1974), N. Nakabayashi, K. Kojima, and E. Masuhara, *J. Bio. Mat. Res.*, 16, 265-273 (1982), K. Nagata, T. F. Lundeen, and P. T. Turner, *J. Bio. Mat. Res.*, 18, 1089-1103 (1984), R. L. Bowen, R. L. Blosser, and A. D. Johnston, Abstract No. 915, p. 276, AIDR/AADR Abstracts 1985 (Paper presented Mar. 22, 1985), E. C. Munksgaard and E. Asmussen, *J. Dent. Res.*, 63, (8): 1087-1089 (1984), E. C. Munksgaard, M. Irie, and E. Asmussen, *J. Dent. Res.*, 64 (12): 1409-1411 (1985), U.S. Pat. Nos. 3,200,142, 4,259,075, 4,259,117, 4,368,043, 4,383,052, 4,443,197, 4,499,251, 4,537,940, and 4,539,382, and Danish Pat. Appl. No. 4898-83.

In addition, many phosphorus-based adhesives have been applied to dentin or enamel. Many of these adhesives have some degree of acidity and may, in some cases, cause mild etching of dentin or enamel. Examples of such adhesives include many of the phosphorus compounds described in the above-mentioned references, as well as those shown in U.S. Pat. Nos. 3,882,600, 3,997,504, 4,182,035, 4,222,780, 4,235,633, 4,404,150, 4,514,342, 4,515,930, 4,544,467, European Published Pat. Appl. Nos. 0 058 483 and 0 155 812, and Japanese Laid-Open Pat. Appl. (Kokai) Nos. 57-14372 and 57-167364.

Several of the above-mentioned references stress that enhanced adhesion to dentin and/or protection from microleakage can be obtained if the pretreatment results in deposition of insoluble calcium salts on the surface of the dentin (see, e.g., U.S. Pat. No. 4,538,990).

A reference of collateral interest to the instant invention, although not itself dealing with the priming of hard tissue, is U.S. Pat. No. 4,525,511. It describes a primer for high solids enamel automotive finishes.

SUMMARY OF INVENTION

The present invention departs in several respects from some of the assumptions that have been made regarding hard tissue adhesives. The invention provides a pretreatment (a primer) that is applied directly to hard tissue. When applied to dentin, it may cause etching of the dentin, but avoids formation of substantial quantities of insoluble calcium salts on the surface of the dentin. The primer enables formation of extremely strong bonds to dentin, exhibiting shear strengths as high as 250 kg/cm$^2$, when tested in shear using the procedure shown in Example 1 of the aforementioned European Published Pat. Appl. No. 0 058 483. Many of the fractured samples fail cohesively within the composite button used in the shear strength test, indicating that the actual strength of the bond to dentin may be even higher than the measured value. Based on work previously carried out in the laboratory of the assignee of this invention, it had been assumed that the cohesive strength of dentin was approximately 100 kg/cm$^2$. Thus the present invention appears to reinforce dentin. Tests to date indicate that an extremely durable adhesive bond with little or no detectable microleakage can be obtained. The primers of the invention can, if desired, be water-based, thus substantially reducing the need to apply them in a dry field.

The present invention provides, in one aspect, a method for adhering to or coating hard tissue, comprising the steps of:

(a) applying to said tissue an acid and a water-soluble film former, without forming adhesively detrimental quantities of calcium salts that are not soluble in said film former, said acid having a pK$_a$ less than or equal to that of phenol and said acid and its calcium salt(s) being soluble in said film former, and (b) hardening said film former.

The present invention also provides novel primer compositions for use in such method, comprising a mixture of said acid and said film former, said mixture being in the form of a film atop said hard tissue.

DETAILED DESCRIPTION

In the practice of the present invention, the hard tissues which can be adhered to or coated include human and animal tissues such as teeth (the component parts of which are enamel, dentin and cementum), bone, fingernails, and hoofs. The invention has particular utility for adhering to or coating dentin and enamel.

The acid and film former can be applied to hard tissue concurrently or sequentially. If they are applied sequentially, then if desired the acid can be rinsed from the hard tissue (e.g., using a water rinse) before application of the film former, or the film former can be applied to the acid without an intermediate rinsing step. Most preferably, the acid and film former are applied concurrently. For brevity, the acid and film former will sometimes be referred to collectively as the "primer".

In a preferred method of the invention, the primer is permitted to stand on the hard tissue for a desired period of time, readily volatile cosolvents are removed therefrom (e.g., by air-drying) to leave a residual film on the surface of the hard tissue, the residual film is overcoated with a layer of additional film former (the additional film former can be water-soluble or water-insoluble but should form a homogeneous solution when combined with the residual film), then the additional film former and residual film are hardened and optionally overcoated with a composite or restorative (hereafter such composites and restoratives will be referred to collectively as "restoratives") or other hardenable coating. Thus the invention enables priming of hard tissue in order to improve the bond strength or durability of a restorative or coating applied thereto.

Acids for use in the present invention can be inorganic or organic acids, and if organic can be monomeric, oligomeric or polymeric. If desired, a precursor to the acid such as an acid anhydride, acid halide (including inorganic acid halides such as Lewis acids and organic acid halides), or ester can be used in place of the acid itself, e.g., to generate the desired acid in situ. Suitable acids include mineral acids, carboxylic acids, sulfonic acids, and phenols, with carboxylic acids, alkylsulfonic acids, and arylsulfonic acids being preferred.

The acid should not form "adhesively detrimental quantities of calcium salts that are not soluble" in the film former. By this is meant that the primer, when lying atop the hard tissue, should be sufficiently free of insoluble calcium salts so that if it is evaluated for shear bond strength according to the procedure of EXAMPLE 1 below, the bond should have an average measured shear strength of at least about 70 kg/cm$^2$, more preferably at least about 120 kg/cm$^2$. For this reason, sulfuric acid, phosphoric acid, citric acid and oxalic acid are undesirable for use in this invention, since their calcium salts are insoluble in the film formers used in the primers of this invention.

The acid has a p$K_a$ in water that is less than or equal to that of phenol, and the acid and its calcium salt (or salts, if the acid is polybasic) are soluble in the film former. Preferably, the p$K_a$ of the acid is between about +10 and about −10, more preferably between about −7 and about +5. A "soluble" acid or calcium salt of an acid, as used herein, is an acid or salt that when mixed with the film former (including any optional cosolvents that are present in the film former) under the desired conditions of use dissolves to form a homogeneous liquid mixture. Such conditions of use include temperature (e.g., body temperature), time (e.g., "standing time", that is, the amount of time the primer is allowed to remain on the surface of the hard tissue before hardening of the film former), and concentration (e.g., the concentration of acid and of calcium salt(s) that may be formed in the film former when the primer is applied to calcium-containing hard tissue such as teeth or bones). An evaluation of the solubility of the acid in the film former can be approximated by observing whether or not a homogeneous solution is formed when the acid is added to pure water, in an amount equivalent to the desired concentration of the acid in the film former. The solubility of the calcium salt(s) of the acid can be similarly approximated by adding slightly less than a stoichiometric amount of a suitable calcium compound (e.g., calcium carbonate) to the resulting acid solution, and observing whether or not a precipitate is formed. Some degree of insolubility of the acid or its calcium salt(s) can be tolerated, but this appears to be detrimental to adhesion. The acid should be sufficiently soluble in the film former to provide the desired degree of adhesion for the particular hard tissue and application involved. For example, on dentin the degree of adhesion preferably is sufficient to provide an average measured shear strength at least 70 kg/cm$^2$, and more preferably at least 120 kg/cm$^2$, when evaluated using the procedure of EXAMPLE 1, below. Preferably, the molar solubility of the calcium salt(s) of the acid is at least as high as that of the acid itself. Acceptable bonding performance on dentin has been obtained using acids whose calcium salt solubility is as low as about $10^{-1}$M, and unacceptable bonding performance on dentin has been obtained using acids whose calcium salt solubility is as high as about $10^{-2}$M. The actual dividing line between acceptable and unacceptable bonding performance probably cannot be precisely expressed in terms of molar solubility of the acid or its calcium salt(s), owing to factors such as the p$K_a$ of the acid.

The acid can be liquid or a solid; if a solid it should be dissolved in a suitable solvent to enable the acid to wet the hard tissue. Liquid acids can also be dissolved in a suitable solvent, e.g., in order to facilitate wetting. Preferred solvents for the acid are the film former cosolvents discussed in more detail below.

Suitable inorganic acids include HBr, HCl, and HNO$_3$. Suitable organic acids include formic acid, trifluoroacetic acid, trichloroacetic acid, dichloroacetic acid, chloroacetic acid, tribromoacetic acid, dibromoacetic acid, bromoacetic acid, acetic acid, α-chloropropionic acid, propionic acid, maleic acid, fumeric acid, citraconic acid, pivalic acid, methacrylic acid, acrylic acid, trihydroxybenzoic acid, benzoic acid, camphorquinonesulfonic acid, camphorsulfonic acid, toluenesulfonic acid, trifluoromethanesulfonic acid, benzenesulfonic acid, 2-hydroxy-4-methoxybenzophenone-5-sulfonic acid, 2-acrylamido-2-methylpropane sulfonic acid, 2-naphthalene sulfonic acid, para-nitrophenol, 2,4-dinitrophenol, and phenol. Mixtures of such acids can be used if desired.

When the acid and film former are applied concurrently, then a preferred amount of acid to be dissolved in the film former will be between about 0.001M and the limit of solubility. The optimum amount depends in part on the p$K_a$ of the acid. For example, for sulfonic acids, concentrations between about 0.01M and about 0.5M are preferred.

The film former is a water-soluble liquid substance or water-soluble liquid mixture of substances, such substance(s) being organic monomers, oligomers, or polymers, being different from the acid, and being capable of forming a hardenable (e.g., polymerizable) continuous or semicontinuous film on the surface of the hard tissue. As used herein, a "water-soluble" film former has a water solubility (exclusive of any water that may be present in the film former) of at least about 5 weight percent. Most preferably, the film former can be mixed with water in all proportions. Preferred film formers contain one or more substances having a sufficient number of water-solubilizing groups such as hydroxyl groups, carboxyl groups, sulfonic acid groups, cationic salts (e.g., ammonium, phosphonium or sulfonium groups), amide linkages or polyether linkages to render the film former water-soluble. The film former preferably wets the hard tissue and most preferably has a sufficiently low viscosity to enable it to flow into interstices that already exist in the surface of the tissue or that are created therein by the action of the acid. To assist in hardening the film former, it preferably contains one or more polymerizable substances. Addition polymerizable substances (e.g., vinyl compounds such as acrylates and methacrylates) are especially preferred. The film former can also contain appropriate polymerization catalysts to assist in hardening the film former.

Preferred film formers include 2-hydroxyethylacrylate, 2-hydroxyethylmethacrylate ("HEMA"), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2-diacrylate and dimethylacrylate, pentaerythritol diacrylate and dimethacrylate, acrylic acid, methacrylic acid, 2-trimethylammonium ethylmethacrylic chloride, 2-acrylamido-2-methylpropanesulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, polyethyleneglycol (400) diacrylate and dimethacrylate, and mixtures thereof.

If the film former is a liquid mixture of substances, then the mixture preferably includes one or more suitable cosolvents. The cosolvent(s) aid in wetting the hard tissue and in solubilizing the acid and its calcium salts. Suitable cosolvents include water, alcohols such as methanol, ethanol, 1-propanol, 2-propanol, and 2-methyl-2-propanol, ketones such as acetone and methyl ethyl ketone, aldehydes such as formaldehyde, acetaldehyde, propionaldehyde, acrolein, glutaraldehyde and 2-hydroxy-adipaldehyde, amides such as acetamide, and other substances such as tetrahydrofuran and dimethyl sulfoxide. The film former preferably contains less than about 95 weight percent cosolvent, more preferably between about 15 and about 85 weight percent cosolvent.

The primer preferably contains only acid and film former. However, if desired other adjuvants such as polymerization catalysts, fluoride compounds, indicators, dyes, wetting agents, buffering agents, thixotropes and the like can be included in the primer, contingent upon attainment of the desired degree of bonding performance and suitability for use on the desired hard tissue.

Hard tissue to which the primer is applied preferably is first cleaned using conventional methods (e.g., by abrading it with a bur), rinsed (e.g., using water) and dried (e.g., using air). If desired, deep excavations in teeth can lined with a conventional basing material (e.g., calcium hydroxide or a glass ionomer cement).

The primer should be allowed to stand on the surface of the hard tissue long enough to provide the desired degree of priming. The standing time will depend upon the particular acid and film former employed, the type of hard tissue and its intended use, and the time available for carrying out the priming procedure. Longer standing times tend to provide better priming. For priming dentin and enamel, standing times less than about 5 minutes, and preferably about 15 seconds to one minute provide very effective priming, although shorter or longer times can be used if desired.

As mentioned above, the primer preferably is overcoated with an optional layer of additional water-soluble or water-insoluble film former, and then hardened. Preferably, such additional film former is copolymerizable with the residual film formed by removal of volatile cosolvents from the primer, and contains a polymerization catalyst (preferably a photoinitiator) capable of hardening the residual film and additional film former. If desired, the additional film former can contain conventional fillers, and can also contain adjuvants of the type described above. A particularly preferred additional film former is obtained by combining the dimethacrylate derived from the reaction between methacrylic acid and the diglycidyl ether of bisphenol A ("Bis-GMA") with a hydrophilic monomer such as HEMA, hydroxypropyl methacrylate, or methacrylic acid. Additional monomers that can be combined with Bis-GMA include tetrahydrofurfural methacrylate, glyceryl-1,3-dimethacrylate, triethyleneglycol dimethacrylate, ethyl methacrylate, n-hexyl methacrylate, polyethyleneglycol dimethacrylate, and 1,6-hexanediol dimethacrylate. The additional film former can also contain cosolvents of the type described above.

Polymerization catalysts that can be included in the primer or in the additional film former are autocure or light cure catalysts such as those mentioned in columns 28 and 29 of U.S. Pat. No. 4,539,382, chromophore-substituted halomethyl-s-triazines such as those shown in U.S. Pat. No. 3,954,475, and chromophore-substituted halomethyl-oxadiazoles such as those shown in U.S. Pat. No. 4,212,970.

As also mentioned above, the primer and optional additional film former preferably are overcoated with a conventional restorative or coating. The hard tissue can then be finished using conventional techniques. For example, on tooth tissue, the primer can be overcoated with a dental adhesive and dental restorative and used, for example, to restore teeth, to install crowns, bridgework or other prosthetic devices, to bond orthodontic brackets to enamel, to seal pits and fissures or to veneer dentin, cementum or enamel. On bone and hoofs, the primer can be used in conjunction with a conventional filled or unfilled bone cement (e.g., a methyl methacrylate-based cement) to repair fractures or to fill defects. On fingernails, the primer can be used in conjunction with a conventional polymerizable fingernail coating to strengthen a fingernail, alter its shape, color or smoothness or fasten an artificial fingernail thereto.

Adhesion to dentin or enamel of the primers of the invention was evaluated as follows:

Five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 320 silicon carbide paper-backed adhesive and then Grade 600 silicon carbide paper-backed abrasive on the lapidary wheel. The polished teeth were stored in distilled water, and used for testing within 2 hours after polishing. The polished teeth were removed from the water and dried using a stream of compressed air. A single drop of primer composition (containing varying amounts of acid, film former and optional water) was painted onto each of the polished tooth surfaces with a brush and allowed to stand for 60 seconds. The primer was then blown dry with compressed air and overcoated with a layer of additional film former. The overcoat was applied with a brush, blown lightly into a film with compressed air and cured using a 20-second irradiation with a "Visilux" dental curing light. Previously prepared molds made from a 2-mm thick "Teflon" sheet with a 4- or 5-mm diameter hole through the sheet were clamped to each polished tooth so that the central axis of the hole in the mold was normal to the polished tooth surface. The hole in each mold was filled with a visible light-curable dental restorative (typically "Silux" brand restorative, universal shade, commercially available from 3M) and cured using a 20-second irradiation. The teeth and molds were allowed to stand for about 5 minutes at room temperature, then stored in distilled water at 37° C. for 24 hours. The molds were then carefully removed from the teeth, leaving a molded button of restorative attached to each tooth.

Adhesive strength was evaluated by mounting the acrylic disk in a holder clamped in the jaws of an "Instron" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed, using a crosshead speed of 2 mm/min.

The following examples are offered to aid in understanding of the present invention and are not to be construed as limiting the scope thereof. Unless otherwise indicated, all parts and percentages are by weight.

EXAMPLE 1

Using the procedure outlined above, the shear strength on dentin of several primer compositions was evaluated. The primers were made from 0.18M solutions of various acids in a 70:30 mixture of HEMA and water. Each primer was overcoated with an additional film former made from a 65:35 mixture of Bis-GMA and HEMA to which had been added 0.25% camphorquinone and 0.5% dimethylaminophenethanol. Set out below in TABLE I are the run number, acid, its pKa, the solubility of the calcium salt of the acid in water, and the average measured adhesive shear bond strength on dentin for each primer.

TABLE I

| Run | Acid | $pK_a$ | $Ca^{++}$ salt solubility, moles of salt per liter of water | Adhesion, $kg/cm^2$ |
|---|---|---|---|---|
| 1 | $H_2SO_4$ | −9 | <0.01 | 0 |
| 2 | HBr | −8 | 7.1 | 119[1] |
| 3 | HCl | −7 | 3.4 | 73[1] |
| 4 | Camphorquinone-10-sulfonic | −6 to −7 | >0.1 | 231[2] |
| 5 | Camphor-10-sulfonic | −6 to −7 | >0.1 | 178[3] |
| 6 | 2-Hydroxy-4-methoxy-benzophenone-5-sulfonic | −6 to −7 | >0.1 | 205 |
| 7 | p-Toluenesulfonic | −6.5 | >0.1 | 198[1] |
| 8 | 2-Acrylamido-2-methylpropane-sulfonic | −5 to −7 | >0.1 | 151 |
| 9 | $HNO_3$ | −1.4 | 5.1 | 146 |
| 10 | 2-Naphthalene-sulfonic | 0.23 | >0.1 | 190[1] |
| 11 | Trifluoroacetic | 0.23 | >0.1 | 194[4] |
| 12 | Trichloroacetic | 0.65 | >0.1 | 230[4] |
| 13 | Tribromoacetic | 0.70 | >0.1 | 243[1] |
| 14 | Oxalic | 1.2 | $5 \times 10^{-5}$ | 42 |
| 15 | Dichloroacetic | 1.48 | >0.1 | 163 |
| 16 | Squaric | — | <0.01 | 51 |
| 17 | Trihydroxybenzoic | 1.70 | >0.1 | 139[1] |
| 18 | Maleic | 1.8 | 0.19 | 233[5] |
| 19 | Citraconic | 1.9 | >0.1 | 129 |
| 20 | $H_3PO_4$ | 2.3 | <<0.01 | 12.6 |
| 21 | α-Chloropropionic | 2.8 | >0.1 | 128 |
| 22 | Chloroacetic | 2.83 | >0.1 | 89 |
| 23 | Citric | 3.1 | 0.0015 | 41 |
| 24 | HF | 32 | 0.0002 | 41[1] |
| 25 | 2,4-Dinitrophenol | 4 | >0.1 | 48[6] |
| 26 | Methacrylic | 4.3 | >0.1 | 90 |
| 27 | Acetic | 4.8 | 0.18 | 96[1] |
| 28 | Pivalic | 5.0 | >0.1 | 65 |
| 29 | Polyacrylic | — | <0.01 | 5 |
| 30 | 2,5-Diaminobenzene-sulfonic | >5 | <0.01 | 41 |
| 31 | N—2-hydroxyethyl-piperazine-N'—2-ethanesulfonic | >5 | <0.01 | 0 |
| 32 | Bromocamphor-8-sulfonic acid ammonium salt | >5 | <0.01 | 29 |
| 33 | p-Nitrophenol | 7.1 | >0.1 | 63 |
| 34 | Phenol | 9.9 | >0.1 | 121 |
| 35 | Control (none) | — | — | 67[7] |

Notes to entries in TABLE I
[1]Average of ten teeth.
[2]Average of 35 teeth.
[3]Average of 25 teeth.
[4]Average of 15 teeth.
[5]Average of 20 teeth.
[6]Yellow color of primer appeared to limit hardening of additional film former by photoinitiator.
[7]Average of 55 teeth.

The above data illustrates the adhesion to dentin obtained when a variety of acids are combined with a film former. Acids whose calcium salts were not soluble in the film former exhibited low adhesion to dentin. Acids having a soluble calcium salt exhibited very high adhesion to dentin. Samples with shear strength values above about 200 kg/cm$^2$ tended to fracture by causing cohesive failure of the dentin or of the restorative button.

EXAMPLE 2

Shelf Stability

A primer composition like that of Run 4 of EXAMPLE 1 (but containing 0.018M acid instead of 0.18M acid) was stored at room temperature for six months and then evaluated for adhesion to dentin. An average measured adhesive shear bond strength of 206 kg/cm$^2$ was observed, indicating that the composition had excellent storage stability.

A primer composition containing 2.2% maleic acid dissolved in a 33:67 mixture of HEMA and water was evaluated for adhesion to dentin using the method of EXAMPLE 1, then stored at 45° C. for 5 days and reevaluated. The initial average measured shear bond strength was 259 kg/cm$^2$, and the value after storage was 239 kg/cm$^2$. This indicated that this composition also should have excellent storage stability.

EXAMPLE 3

Microleakage

Two evaluators excavated a box-shaped Class V preparation at the dentin-enamel junction of five human teeth. Each prepared cavity was thoroughly rinsed with water and dried with air, followed by etching the freshly exposed enamel for 30 seconds using gelled 37% σ-phosphoric acid. The etched enamel was rinsed with water for 15 seconds and dried with air. The primer of Run 4 of EXAMPLE 1 was applied to the prepared cavity and allowed to stand for 60 seconds, then dried with air. The primed, prepared cavity was overcoated with a 65:35 mixture of Bis-GMA and HEMA containing 0.25% camphorquinone and 0.5% dimethylaminophenethanol and cured for 20 seconds using a "Visilux" curing light (3M). The prepared cavity was filled with "Silux" brand restorative, universal shade (3M) and cured for 20 seconds.

The filled teeth were thermocycled in water for 500 cycles between 12° and 50° C. Nail polish was painted to within 1 mm of each restoration (and exposed root ends, if present, were plugged with "Silux" restorative and light-cured) to isolate the restoration. The teeth were soaked in 50% silver nitrate solution for 2 hours, thoroughly rinsed, then soaked in photographic developer solution for at least four hours under a fluorescent desk lamp. The teeth were rinsed, partially embedded in circular acrylic disks, and sectioned with a diamond saw through the center of the restoration. The degree of microleakage was rated by evaluating the penetration of silver stain along the dentin wall of the cavity using the following scale:

0 = no penetration.
1 = penetration one fourth of the way down the cavity wall.
2 = penetration one half of the way down the cavity wall.
3 = penetration three fourths of the way down the cavity wall.
4 = penetration all of the way down the cavity wall.
5 = penetration extending into the floor of the cavity.

A rating of 0.7 was observed. This represents the lowest microleakage rating observed to date in the laboratory of the assignee of this invention, based on evaluations using this test on many commercial and experimental dental adhesives and primers. The result indicates that the restoration should exhibit a minimal "contraction gap" (space between the restoration and the tooth created by polymerization shrinkage of the restorative) and good clinical performance.

EXAMPLE 4

Adhesion to Enamel Without $H_3PO_4$ Etching

The composition of Run 4 of Example 1 was applied to unetched enamel and allowed to stand for 60 seconds. Without rinsing off the primer, the overcoat of additional film former used in EXAMPLE 1 was applied to the primer-coated tooth enamel. An average measured adhesive shear bond strength of 209 kg/cm$^2$ was obtained, a value which compares very favorably to the value of 235 kg/cm$^2$ obtained when a conventional acid etching procedure (a 60 second etch with gelled 37% $\sigma$-phosphoric acid, a water rinse, and a jet of air to dry the tooth) was used in place of the primer composition. This indicates that the composition of this invention will permit bonding to enamel without the need for phosphoric acid etching.

EXAMPLE 5

To illustrate the effect of variation in the amount of acid, six primer solutions containing varying amounts of methacrylic acid and optionally HEMA or water were applied to dentin and evaluated using the method of EXAMPLE 1. Set out below in TABLE II are the run number, amount of acid, HEMA, and water and the average measured adhesive shear bond strength on dentin.

TABLE II

| Run | Primer ingredients, parts | | | Adhesion, kg/cm$^2$ |
| --- | --- | --- | --- | --- |
| | Acid | HEMA | Water | |
| 1 | 0 | 70 | 30 | 67 |
| 2 | 5 | 66.5 | 28.5 | 90 |
| 3 | 7 | 93 | 0 | 63 |
| 4 | 15 | 0 | 85 | 56 |
| 5 | 70 | 0 | 30 | 161 |
| 6 | 100 | 0 | 0 | 96 |

The above data indicates that good bonding performance can be obtained even when the acid and separate film former are applied in different layers. It is believed that some of the primer solutions (e.g., Runs 3 and 4) would have provided higher bond strengths if longer standing times had been employed.

EXAMPLE 6

To illustrate further the effect of variation in the amount of acid, six primer solutions containing varying amounts of camphorquinone-10-sulfonic acid in a 70:30 mixture of HEMA and water were applied to dentin and then overcoated with one of two additional film formers. Overcoat "A" contained a 50:50 mixture of Bis-GMA and triethyleneglycol dimethacrylate, and Overcoat "B" contained a 65:35 mixture of Bis-GMA and HEMA. Each overcoat contained 0.25% camphorquinone and 0.5% dimethylaminophenethanol. Set out below in TABLE III are the run number, amount of acid, and the average measured adhesive shear bond strength on dentin for each overcoat.

TABLE III

| Run | % Acid | Adhesion, kg/cm$^2$ | |
| --- | --- | --- | --- |
| | | Using Overcoat A | Using Overcoat B |
| 1 | 0 | 80 | 90 |
| 2 | 1.0 | 130 | 169 |
| 3 | 2.0 | 136 | 201 |
| 4 | 3.5 | 101 | 227 |
| 5 | 5.0 | — | 256 |
| 6 | 10.0 | — | 143 |

The above data illustrates that the optimum concentration of acid depends in part upon the composition of the overcoat. The best performance using Overcoat A was observed with a primer containing about 2% acid, while the best performance with Overcoat B was observed with a primer containing about 5% acid.

EXAMPLE 7

To illustrate the effect of variation in the amount of water in the film former, seven primer solutions containing 5% camphorquinone-10-sulfonic acid and varying amounts of HEMA and/or water were applied to dentin. Set out below in TABLE IV ae the run number, amount of HEMA and/or water, and the average measured adhesive shear bond strength (average of ten samples) on dentin.

TABLE IV

| Run | HEMA, parts | Water, parts | Adhesion, kg/cm$^2$ |
| --- | --- | --- | --- |
| 1 | 0 | 95 | 41 |
| 2 | 14 | 81 | 147 |
| 3 | 29 | 66 | 186 |
| 4 | 43 | 52 | 187 |
| 5 | 57 | 38 | 190 |
| 6 | 71 | 24 | 172 |

TABLE IV-continued

| Run | HEMA, parts | Water, parts | Adhesion, kg/cm² |
|---|---|---|---|
| 7 | 85 | 10 | 168 |

The above data indicates that optimum bond strength is obtained when the acid and film former are applied concurrently, and when the primer composition contains water.

EXAMPLE 8

To illustrate the effect of variation in the composition of the overcoat of additional film former, a series of overcoat compositions were applied to one of two different primers, and evaluated for adhesion to dentin. Primers "A" and "B" contained a 70:30 HEMA:water mixture to which had been added 3.5% and 2%, respectively, of camphorquinone-10-sulfonic acid. Set out below in TABLE V are the run number, identity of the primer, ingredients in the overcoat and the average measured adhesive shear bond strength on dentin.

TABLE V

| Run | Primer | Overcoat ingredients, parts[1] | | | | | Adhesion, kg/cm² |
|---|---|---|---|---|---|---|---|
| | | Bis-GMA | HEMA | PEGDMA[2] | DUDM[3] | ITM[4] | |
| 1 | A | 65 | 35 | — | — | — | 199 |
| 2 | A | 65 | 25 | 10 | — | — | 199 |
| 3 | A | 65 | 10 | 25 | — | — | 202 |
| 4 | A | 65 | 0 | 35 | — | — | 151 |
| 5 | A | 55 | 35 | 15 | — | — | 170 |
| 6 | A | 55 | 15 | 35 | — | — | 205 |
| 7 | B | 65 | 35 | — | — | — | 184 |
| 8 | B | 55 | 30 | 15 | — | — | 246 |
| 9 | B | — | 35 | — | 65 | — | 191 |
| 10 | B | — | 30 | 15 | 55 | — | 131 |
| 11 | B | — | 30 | 15 | — | 55 | 166 |

Notes to entries in TABLE V
[1]Each overcoat also contained 0.5% dimethylaminophenethanol and 0.25% camphorquinone.
[2]Polyethyleneglycol (400) dimethacrylate ("MFM-109", Rohm Tech Inc.)
[3]Diurethane dimethacrylate ("6661-0", Rohm Tech Inc.)
[4]Tris(methacryloxypropyl) isocyanurate.

EXAMPLE 9

To illustrate the effect of altering the viscosity of the overcoat and diluting it with water-miscible solvent, five overcoat compositions containing varying amounts of Bis-GMA, HEMA, and optionally ethanol were applied to dentin and evaluated for adhesion using the primer of Run 4 of EXAMPLE 1. Set out below in TABLE VI are the run number, ingredients in the overcoat and the average measured adhesive shear bond strength on dentin.

TABLE VI

| Run | Overcoat ingredients, parts[1] | | | Adhesion, kg/cm² |
|---|---|---|---|---|
| | Bis-GMA | HEMA | Ethanol | |
| 1 | 80 | 20 | — | 126 |
| 2 | 75 | 25 | — | 226 |
| 3 | 65 | 35 | — | 202 |
| 4 | 56 | 14 | 30 | 161 |
| 5 | 53 | 17 | 30 | 218 |

Notes to entries in TABLE VI
[1]Each overcoat also contained 0.5% dimethylaminophenethanol and 0.25% camphorquinone.

EXAMPLE 10

Varying amounts of maleic acid were dissolved in a mixture containing varying amounts of HEMA and/or water, applied to dentin or unetched enamel, and evaluated for adhesion. Set out below in TABLE VII are the run number, percent acid, relative amounts of HEMA and water, and the average measured adhesive shear bond strength on dentin and enamel.

TABLE VII

| Run | % Acid | Relative amounts of HEMA and WATER, parts | | Adhesion, kg/cm² | |
|---|---|---|---|---|---|
| | | HEMA | Water | Dentin | Enamel |
| 1 | 0.56 | 0 | 100 | 16.2 | 120.7 |
| 2 | 0.56 | 33 | 67 | 162.8 | 104.7 |
| 3 | 0.56 | 67 | 33 | 52.7 | 100.0 |
| 4 | 0.56 | 100 | 0 | 32.4 | 54.4 |
| 5 | 1.12 | 0 | 100 | 21.9 | 190.4 |
| 6 | 1.12 | 33 | 67 | 269.3 | 105.8 |
| 7 | 1.12 | 67 | 33 | 214.8 | 120.1 |
| 8 | 1.12 | 100 | 0 | 43.5 | 72.5 |
| 9 | 2.24 | 0 | 100 | 20.8 | 155.2 |
| 10 | 2.24 | 33 | 67 | 253.4 | 178.8 |
| 11 | 2.24 | 67 | 33 | 227.1 | 119.0 |
| 12 | 2.24 | 100 | 0 | 43.5 | 66.0 |
| 13 | 4.40 | 0 | 100 | 36.3 | 159.0 |
| 14 | 4.40 | 33 | 67 | 104.0 | 216.2 |
| 15 | 4.40 | 67 | 33 | 188.6 | 130.9 |
| 16 | 4.40 | 100 | 0 | 53.8 | 67.2 |

Various modifications and alterations of this invention will be apparent to those skilled in the art without departing from the scope and spirit of this invention, and it should be understood that this invention is not limited to the illustrative embodiments set forth herein.

We claim:

1. A method for adhering to or coating dentin, comprising the steps of:
   (a) applying to said dentin adhesively effective amounts of an acid and a water-soluble film former, without forming adhesively detrimental quantities of calcium salts that are not soluble in said film former, said acid having a $pK_a$ less than or equal to that of phenol and said acid and its calcium salt(s) being soluble in said film former, and
   (b) hardening said film former.

2. A method according to claim 1, wherein water, said acid and said film former are concurrently applied as an aqueous mixture to said dentin.

3. A method according to claim 1, wherein said acid has a $pK_a$ between about −10 and about +10.

4. A method according to claim 2, wherein said acid has a $pK_a$ between about −7 and about +5.

5. A method according to claim 1, wherein said calcium salt(s) of said acid have a solubility in said film former of at least about $10^{-1}$ M.

6. A method according to claim 1, wherein said acid comprises carboxylic acid.

7. A method according to claim 1, wherein said acid comprises sulfonic acid.

8. A method according to claim 1, wherein said acid is selected from the group consisting of alkylsulfonic acids, arylsulfonic acids, trifluoroacetic acid, trichloroacetic acid, tribromoacetic acid and maleic acid.

9. A method according to claim 1, wherein said film former contains one or more substances having a sufficient number of water-solubilizing groups to render said film former, exclusive of any water that may be present therein, soluble in water to at least 5 weight percent, such water-solubilizing groups being selected from hydroxyl groups, carboxyl groups, sulfonic acid groups, cationic salts, amide linkages and polyether linkages.

10. A method according to claim 1, wherein said film former contains one or more addition-polymerizable substances having one or more hydroxyl groups, carboxyl groups or sulfonic acid groups.

11. A method according to claim 1, wherein said film former comprises a mixture of 2-hydroxyethylmethacrylate and water.

12. A method according to claim 2, wherein said acid has a $pK_a$ between about $-7$ and about $+5$, said calcium salt(s) of said acid have a solubility in said film former of at least about $10^{-1}M$, said film former contains one or more addition-polymerizable substances having one or more hydroxyl groups, and prior to hardening said film former, readily volatile solvents are removed therefrom to leave a residual film that is then overcoated with an additional film former that forms a homogeneous solution when combined with said residual film, said residual film and said additional film former being hardened using an autocuring or lightcuring polymerization catalyst.

13. A method according to claim 12, wherein said additional film former comprises a copolymerizable mixture of Bis-GMA and a hydrophilic monomer selected from the group consisting of 2-hydroxyethylmethacrylate, hydroxypropylmethacrylate and methacrylic acid, and said polymerization catalyst comprises a photoinitiator.

14. A primer film, said film lying on the surface of hard human or animal tissue, and comprising a mixture of adhesively effective amounts of an acid and a water-soluble film former, said acid having a $pK_a$ less than or equal to that of phenol and said acid and its calcium salt(s) being soluble in said film former, said mixture being free of adhesively detrimental quantities of calcium salts that are not soluble in said film former.

15. A film according to claim 14, wherein said acid has a $pK_a$ between about $-10$ and about $+10$.

16. A film according to claim 14, wherein said acid has a $pK_a$ between about $-7$ and about $+5$.

17. A film according to claim 14, wherein said acid is selected from the group consisting of alkylsulfonic acids, arylsulfonic acids, trifluoroacetic acid, trichloroacetic acid, tribromoacetic acid, and maleic acid.

18. A film according to claim 17, wherein said film former comprises hydroxyethylmethacrylate and one or more cosolvents selected from the group consisting of water, alcohols, ketones, aldehydes, and amides.

19. A method according to claim 1, wherein said acid comprises maleic acid.

20. A film according to claim 14, wherein said acid comprises maleic acid.

21. A method for adhering to or coating hard human and animal tissue, comprising the steps of:
(a) concurrently applying to said issue a mixture of adhesively effective amounts of acid and water-soluble film former, without forming adhesively detrimental quantities of calcium salts that are not soluble in said film former, said acid having a $pK_a$ less than or equal to that of phenol and said acid and its calcium salt(s) being soluble in said film former, and
(b) hardening said film former.

22. A method according to claim 21, wherein said mixture further comprises water and said acid is selected from the group consisting of alkylsulfonic acids, arylsulfonic acids, trifluoroacetic acid, trichloroacetic acid, tribromoacetic acid and maleic acid.

* * * * *

UNITED STATES PATENT AND TRADEMARK OFFICE
CERTIFICATE OF CORRECTION

PATENT NO. : 4,719,149

DATED : January 12, 1988

INVENTOR(S) : Steven M. Aasen and Joel D. Oxman

It is certified that error appears in the above-identified patent and that said Letters Patent is hereby corrected as shown below:

Column 3, line 11, replace "percursor" with ---precursor---.

Column 10, line 57, replace "ae" with --are--.

Column 14, line 27, replace "issue" with --tissue--.

Signed and Sealed this

Thirty-first Day of January, 1989

Attest:

DONALD J. QUIGG

Attesting Officer

Commissioner of Patents and Trademarks